United States Patent
Dysarz (10) Patent No.: US 6,186,979 B1
(45) Date of Patent: Feb. 13, 2001

(54) ONE-HANDED RETRACTABLE BLOOD COLLECTION DEVICE WITH TRAP-IN CONTAINER

(76) Inventor: Edward D. Dysarz, 11423 Triola La., Houston, TX (US) 77072

( * ) Notice: Under 35 U.S.C. 154(b), the term of this patent shall be extended for 0 days.

(21) Appl. No.: 09/039,402

(22) Filed: Mar. 16, 1998

(51) Int. Cl.$^7$ ............................................... A61M 5/00
(52) U.S. Cl. .......................... 604/110; 128/898; 600/576; 604/263
(58) Field of Search ...................... 600/573, 576; 128/898, 919; 604/110, 192, 263; 43/20

(56) References Cited

U.S. PATENT DOCUMENTS

| | | | |
|---|---|---|---|
| 3,008,570 | 11/1961 | Roehr et al. | 206/43 |
| 3,107,785 | 10/1963 | Roehr et al. | 206/63.2 |
| 3,306,291 | 2/1967 | Burke | 128/218 |
| 3,895,633 | 7/1975 | Bartner et al. | 128/218 DA |
| 4,266,544 * | 5/1981 | Wardlaw | 604/110 |
| 4,300,678 | 11/1981 | Gyure et al. | 206/364 |
| 4,356,822 | 11/1982 | Hall | 128/215 |
| 4,425,120 | 1/1984 | Sampson | 604/198 |
| 4,634,428 * | 1/1987 | Cuu | 604/110 |
| 4,639,249 | 1/1987 | Larson | 604/198 |
| 4,655,751 | 4/1987 | Harbaugh | 604/198 |
| 4,664,654 | 5/1987 | Strauss | 604/198 |
| 4,840,619 | 6/1989 | Hughes | 604/187 |
| 5,002,533 * | 3/1991 | Jullien | 604/110 |
| 5,019,048 * | 5/1991 | Margolin | 604/153 |
| 5,084,019 * | 1/1992 | Gartz | 604/110 |
| 5,084,020 * | 1/1992 | Gartz | 604/110 |
| 5,242,400 * | 9/1993 | Blake, III et al. | 604/110 |
| 5,328,484 * | 7/1994 | Somers et al. | 604/195 |
| 5,476,106 * | 12/1995 | Gartz | 128/898 |
| 5,522,833 * | 6/1996 | Stephens et al. | 606/185 |

* cited by examiner

Primary Examiner—Cary O'Connor
Assistant Examiner—Charles Marmor, II (57) ABSTRACT

A blood collection device combining an elongated needle cannula and vial insertion cannula fixed to a rotatable reel. The rotatable reel is supported in an L-shaped bowl and hollow stem combination. A sloping needle cannula is injected into a body or vein inside of a body so blood or other fluid flows from the body into the needle cannula and into the vial insertion cannula. A vial is inserted into the bowl until the vial insertion cannula penetrates the soft vial plug and the vial then is filled with blood or other fluid. When sufficient blood or fluid is drawn into the vial, the vial is removed and a lever or button is pushed, releasing a biased coil spring which causes the reel to rotate, thus winding the needle cannula and the vial insertion cannula around the reel, destroying the needle cannula and the vial insertion cannula and further pulling the needle cannula into the hollow stem and the vial insertion cannula into the bowl, preventing a person from being accidentally pricked or otherwise injured by either contaminated cannula.

8 Claims, 7 Drawing Sheets

ONE-HANDED RETRACTABLE BLOOD COLLECTION DEVICE WITH TRAP-IN CONTAINER

BACKGROUND OF INVENTION

There are several types of safety blood sampling designs available today. One such design is shown in a patent issued to Jagger et al on Jun. 3, 1986 U.S. Pat. No. 4,592,744. This is a safety blood sampling device that requires two hands to operate or to cover the needle cannula.

Blood samples are also taken with syringes and there are also many safety syringes available. Some of these designs have a sleeve or sheath that will cover the needle after it has been used. Some typical designs with sleeves or sheaths are Z. M. Roehr et al., U.S. Pat. No. 3,008,570; Z. M. Roehr, U.S. Pat. No. 3,107,785; Bartner et al., U.S. Pat. No. 3,895,633; G. K. Burke, U.S. Pat. No. 3,306,291; Gyure et al., U.S. Pat. No. 4,300,678; Winstead Hall, U.S. Pat. No. 4,356,822; Sampson, U.S. Pat. No. 4,425,120; Larson, U.S. Pat. No. 4,639,249; Harbaugh, U.S. Pat. No. 4,655,751; Strauss, U.S. Pat. No. 4,664,654; Braginetz, U.S. Pat. No. 4,666,435; Spencer, U.S. Pat. No. 4,702,738; Milorad, U.S. Pat. No. 4,702,739; Spencer, U.S. Pat. No. 4,801,295; Poncy, U.S. Pat. No. 4,816,022; and Hughes, U.S. Pat. No. 4,840,619.

Other designs have a retractable needle such as Weltman, U.S. Pat. No. 3,306,290; and Dent, U.S. Pat. No. 4,392,859. These designs do not have a means whereby the needle is extended from the syringe and held in place in a positive and rigid position in order to first inject the needle prior to injecting the medication. Still other designs have methods of bending the needle to render it harmless after the medication has been injected. Most of these designs have one major purpose and that is to prevent the spread of infectious diseases such as aids, hepatitis, or other diseases from accidental injection with a contaminated needle after the needle of the syringe has been inserted into a patient with the above mentioned disease. These various designs all work well to a degree, but they all fall short of their intended purpose during the act of covering the needle, or removing the needle, which requires two hands.

All of these designs require at least two hands to operate. The use of two hands to cover the contaminated needle is most unsatisfactory in that during the act of placing a second hand on the blood sampling device or syringe, the person holding the blood sampling device or syringe in one hand may be bumped and accidentally inject the needle into their other hand before it can grasp the syringe. Other accidental jabbings or injections can happen in an ambulance where just as a person tries to grasp the contaminated blood sampling device or syringe, the ambulance can hit a bump in the road causing the person holding the blood sampling device or syringe to accidentally stick another person or themselves with the contaminated needle. The need has developed for a blood sampling device or syringe that will cover the contaminated needle with the use of only one hand.

SUMMARY

It is the object of this invention to provide a blood sampling device wherein the needle of the blood sampling device is retracted into the barrel of the blood sampling device to protect others from an accidental pricking after it has been used. The needle cannula can be retracted into the barrel with the use of only one hand; and that one hand being the hand that was used to inject the needle cannula into a patient. It is still another object of the present invention to further prevent the accidental release of the needle cannula after the needle cannula is in the barrel of the blood sampling device. It is still yet another object of the present invention to provide a blood sampling device wherein the needle cannula is sloped for ease of skin penetration.

The foregoing and other objects and advantages are attained by a blood sampling device. Another object of the present invention is to render the blood sampling device useless after the needle cannula is retracted into the barrel of the blood sampling device to prevent the accidental reuse of the contaminated device. This is accomplished using a hollow sloping cannula guide, a needle cannula, a reel, a biased spring and a vial guide tube in combination with a latching means, wherein when said blood sampling device is used to inject a needle cannula into a vein in the body or part of the body in order to withdraw blood for testing purposes, the latching means is released and the biased spring rotates the reel and further winds the needle cannula and the vial insertion cannula around said reel thereby rendering the needle cannula and the vial insertion cannula harmless and preventing the accidental pricking of others.

The features of the present invention can be best understood together with further objects and advantages by reference to the following descriptions taken in connection with accompanying drawing, wherein like numerals indicate like parts.

DETAILED DESCRIPTION OF THE PREFERRED EMBODIMENT

Figure 1:
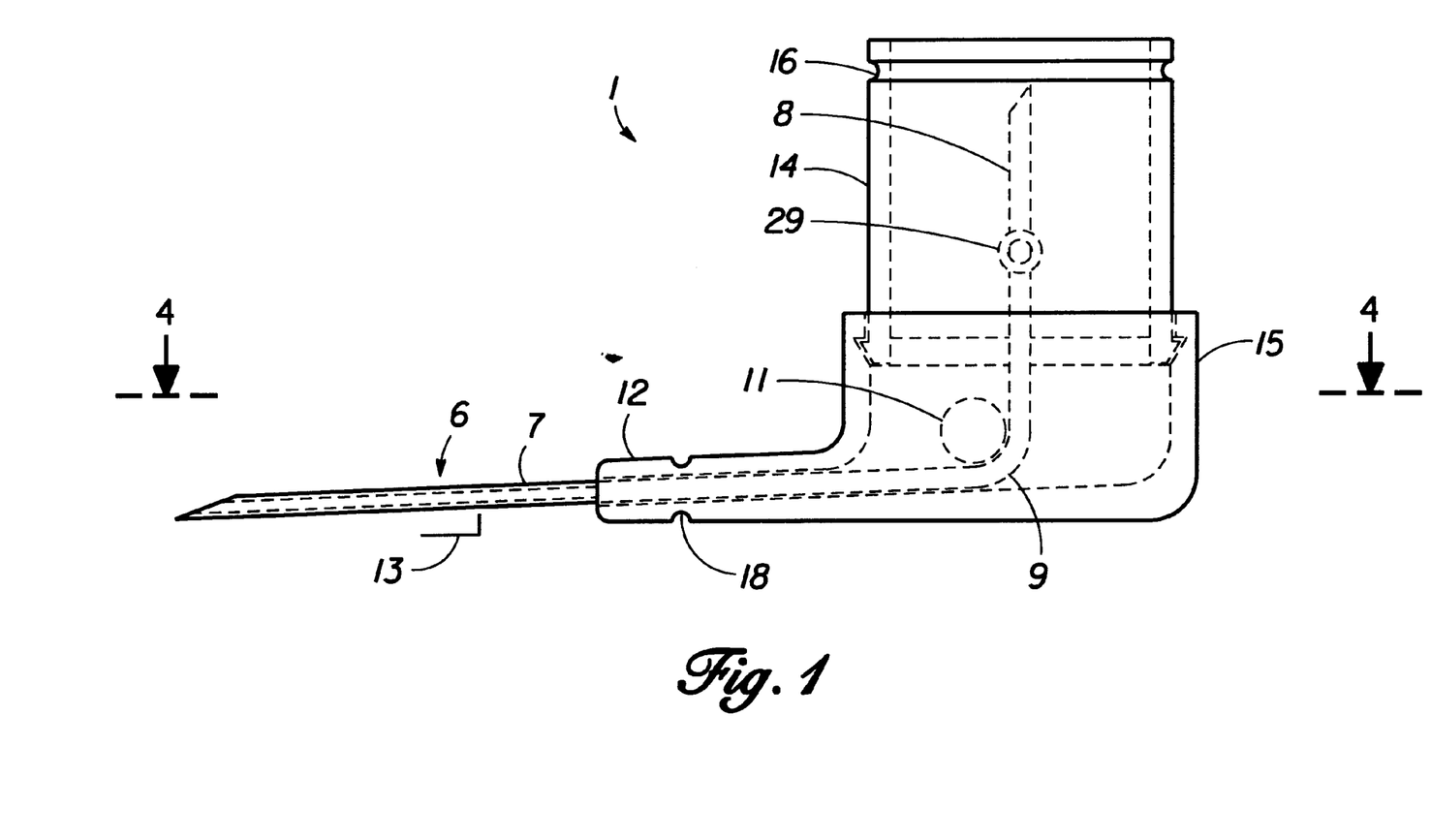
FIG. 1 is an elevational view of the preferred embodiment.

Referring to FIG. 1 there is shown an exterior elevational view of the device 1 of the preferred embodiment.

The cannula 6 is shown comprised of three sections: the needle cannula 7 that is the section of the cannula 6 that is inserted into a body, the cannula bend 9 is the section that is suitably bent around the bend bar 11, and the vial insertion cannula 8 or the part of the cannula 6 that is inserted into a blood collection vial.

The needle cannula guide 12 has a first end wherein the needle cannula 7 extends from the first end of the needle cannula guide 12. The needle cannula 7 is shown extending from the needle cannula guide 12 at a slight declivity 13. The declivity 13 allows the needle cannula 7 to be inserted into the flesh, veins, or arteries easier and to remain in the flesh with less stress on the flesh. The needle cannula guide has a second end that forms an elbow and a receptor 15 for the vial guide tube 14. The third end of the needle cannula guide 12 rests on part of the flesh that is penetrated by the needle cannula 7, and the fourth end is the area of the needle cannula guide 12 that forms the receptor 15 for the vial guide tube 14. The first end of the receptor 15 is where the needle cannula guide 12 rests on the flesh of a body, the second end of the recepter receives the vial guide tube 14.

The first end of the vial guide tube 14 is inserted into the fourth end of the needle cannula guide 12 and the second end of the vial guide tube 14 is open to receive the vial. The vial guide tube 14 covers the vial insertion cannula 8 to prevent an accidental pricking from the vial insertion cannula.

The guide tube indentation 16 is formed near the second end of the vial guide tube 14 to allow a guide tube cap to cover the second end of the vial guide tube 14 to maintain sterility. The needle cannula guide indentation 18 is for the needle cannula cap that will protect the needle cannula 7 during packaging storage and handling prior to use.

Figure 2:
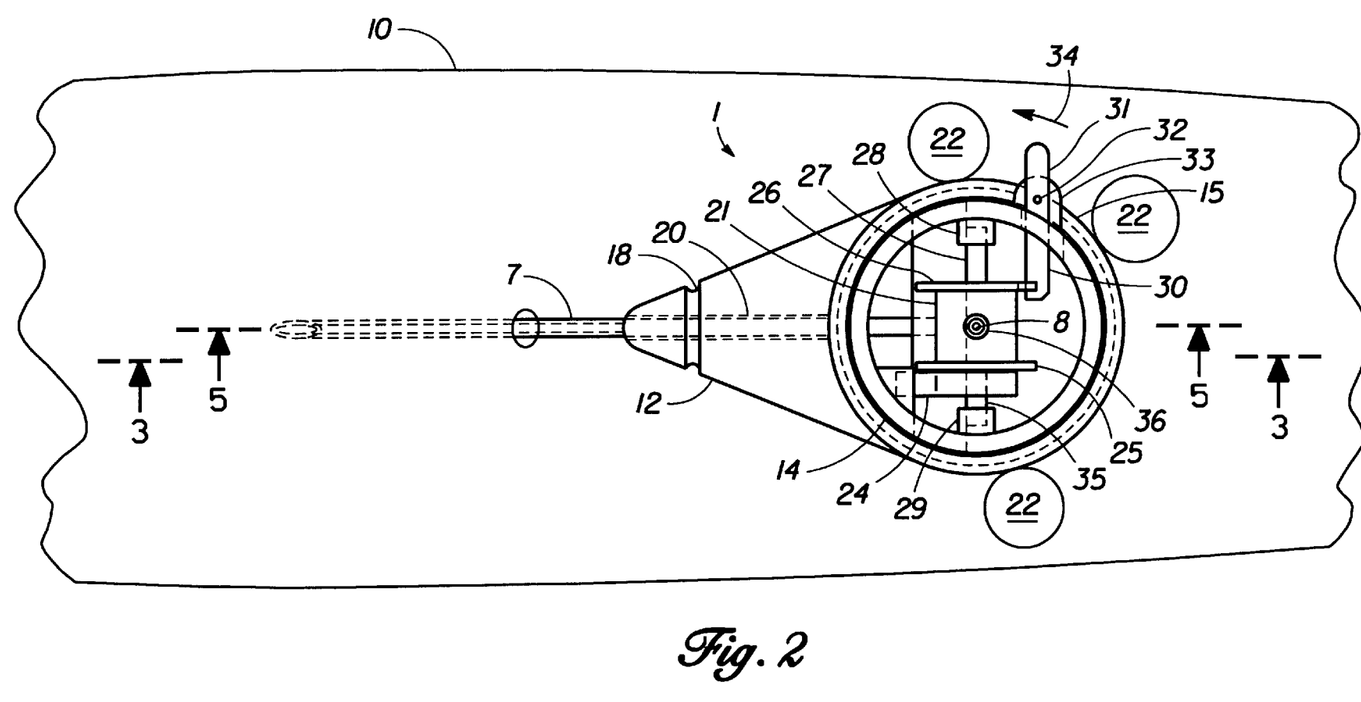
FIG. 2 Is a plan view of the preferred embodiment.

Referring to FIG. 2 there is shown a plan view of the device 1 with the needle cannula 6 inserted into a body 10. The needle cannula guide 12 is shown supporting the needle cannula 7. A guide tunnel 20 is formed within the needle cannula guide 12 that is slightly larger than the outside diameter of the needle cannula 7 to allow the needle cannula 7 to be pulled through the guide tunnel 20 and still be supported laterally by the guide tunnel 20.

The second end of the needle cannula guide 12 is shown formed into a receptor 15 for the vial guide tube 14. The third end of the needle cannula guide 12 is at the lower end of the receptor 15 and the fourth end of the needle cannula guide 12 and receptor 15 is open to receive the vial guide tube 14. Three fingers 22 or two fingers and a thumb are shown holding the device 1.

Inside the vial guide tube 14 there is shown the cannula reel 21 with a first rim 25 and a second rim 26. An axle 27, with a first end and a second end, is suitably fixed to the first rim 25 and the second rim 26. The first end of the axle 27 is disposed in the first socket 28 and the second end of said axle 27 is disposed in said second socket 29. The cannula reel 21, the first axle 27 and a second axle 35, each with a first end and a second end, rotate freely and in said first socket 28 in said second socket 29 and are held in place by the first socket 28 and the second socket 29 when the reel stop 30 releases the second rim 26. The first socket 28 and the second socket 29 are hollow tubes formed on the inside wall of the vial guide tube 14 between the first end and the second end of the vial guide tube 14.

The reel stop 30 is inserted into a notch not seen in this view that is formed in the second rim 26 and prevents the second rim 26, the first rim 25, and the cannula reel 21 from rotating. The reel stop 30 is rotatably fixed to the reel stop support 33 by a pivot pin 32. The reel stop 30 is released from the second rim 26 by pressing on the finger tab 31 in the release direction 34. The first rim 25 has a first side and a second side. The second rim 26 has a first side and a second side.

The vial insertion cannula 8 is shown suitably disposed in a hole 35 formed in the cannula reel 21. The first end of the cannula reel 21 is fixed to the second side of the first rim 25 and the second end of the cannula reel 21 is fixed to the first side of the second rim 26. The cannula reel 21 will rotate as will be seen in FIG. 7 and will bend the vial insertion cannula 8 about the cannula reel 21 thereby destroying the needle cannula 7 and the vial insertion cannula 8.

Figure 3:
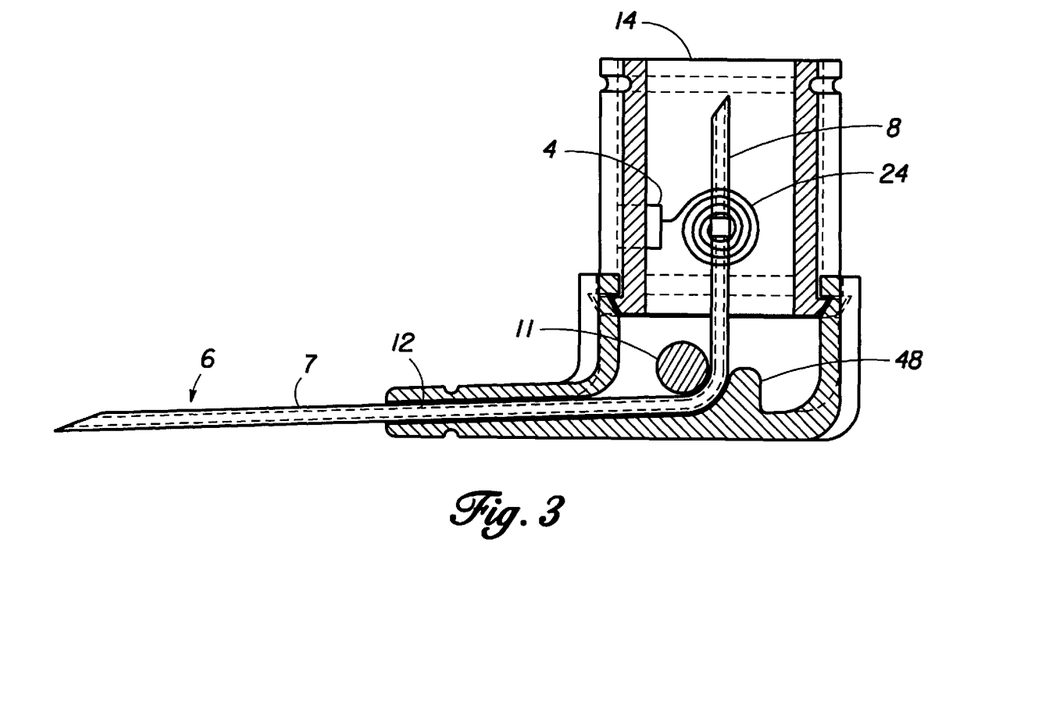
FIG. 3 is a sectional elevational view as taken along line 3—3 of FIG. 2.

Referring to FIG. 3 there is shown a sectional elevational view of the device 1 as taken through line 3—3 of FIG. 2.

The first end of the cannula 6 referred to as the needle cannula 7 and the second end of the cannula 6 is the vial insertion cannula 8. The cannula 6 extends into the needle cannula guide 12 and is further bent around the bend bar 1I1 wherein the second end of the cannula 6 becomes the vial insertion cannula 8 and is disposed in a hole formed in the cannula reel 21 wherein the vial insertion cannula 8 extends into and is disposed inside of the vial guide tube 14 and extends near the second end of the vial guide tube 14.

The first end of the biased spring 24 is shown suitably fixed to the spring stop 4. The second end of the biased spring 24 is suitably fixed to the axle 27. As the first end of the needle cannula 7 is inserted into flesh, the needle cannula 7 may thrust back; to prevent this thrust, a cannula thrust stop 48 is shown backing up the cannula 6 at the cannula bend 9.

Figure 4:
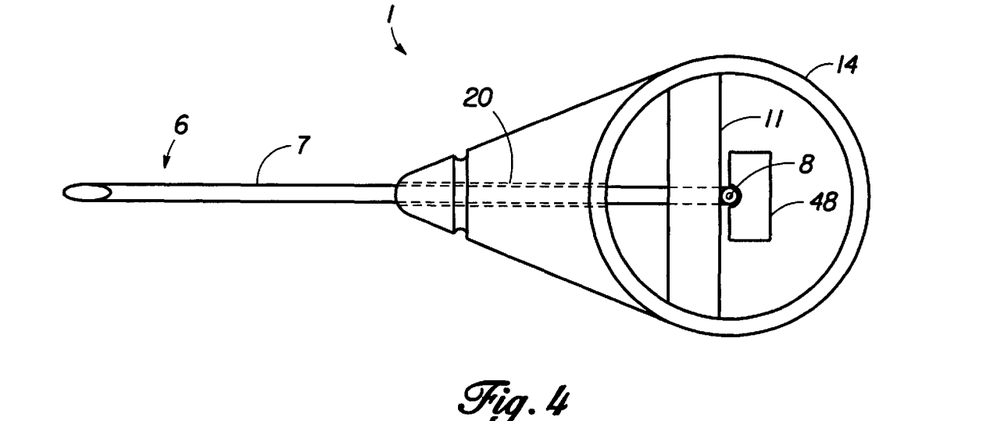
FIG. 4 Is a sectional plan view as taken along line 4—4 of FIG. 1.

Referring to FIG. 4 there is shown a sectional plan view of the device 1 as taken through line 4—4 of FIG. 1.

The needle cannula 7 is shown extending into the needle cannula guide 12 and is disposed in the guide tunnel 20 wherein the needle cannula is bent around the bend bar 11 and turns into the vial guide tube 14, wherein the second end of the cannula 6 is referred to as the vial insertion cannula 8. The cannula thrust stop 48 is shown backing the cannula 6.

Figure 5:
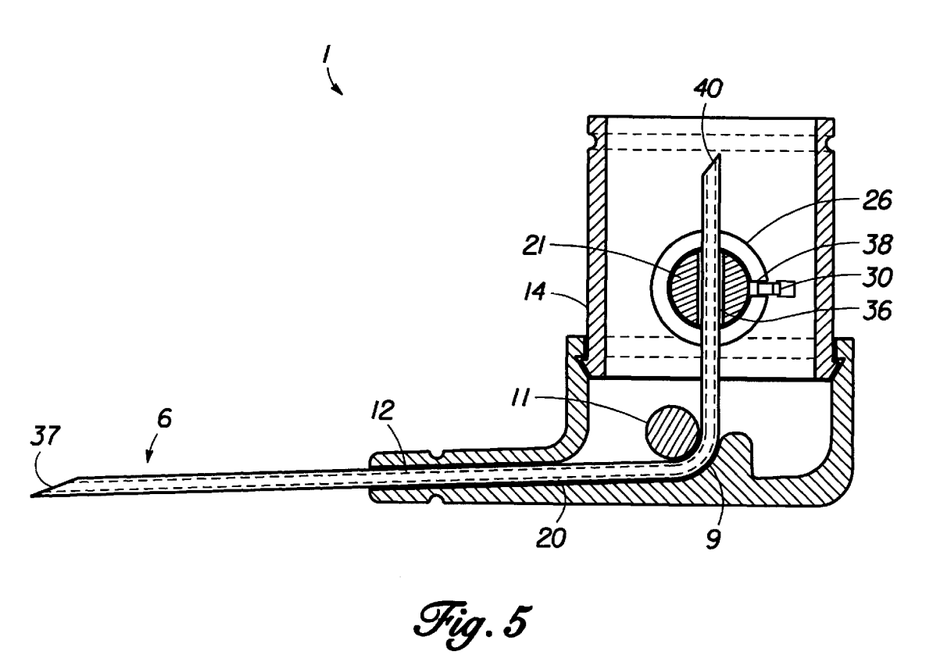
FIG. 5 is another sectional elevational view as taken along line 5—5 of FIG. 2.

Referring to FIG. 5 there is shown a sectional elevational view of the device 1 as taken through line 5—5 of FIG. 2.

The needle cannula 7 is shown disposed in the guide tunnel 20 of the needle cannula guide 12. The cannula 8 is further bent around the bend bar 1I1 and extends toward the vial guide tube 14 and is disposed in the hole 36 formed in the cannula reel 21. The hole formed in the cannula reel 21 extends from the third side of the cannula reel 21 to the fourth side of the cannula reel 21. The first end of the of the cannula 6 is shown with a first point 37. The second end of the cannula 6 is shown with a second point 40.

The second rim 26 is shown with a slot 38 formed that extends from the first side to the second side of the second rim 26. The reel stop 30 is shown suitably inserted into the slot 38, to prevent the cannula reel 21 from rotating.

Figure 6:
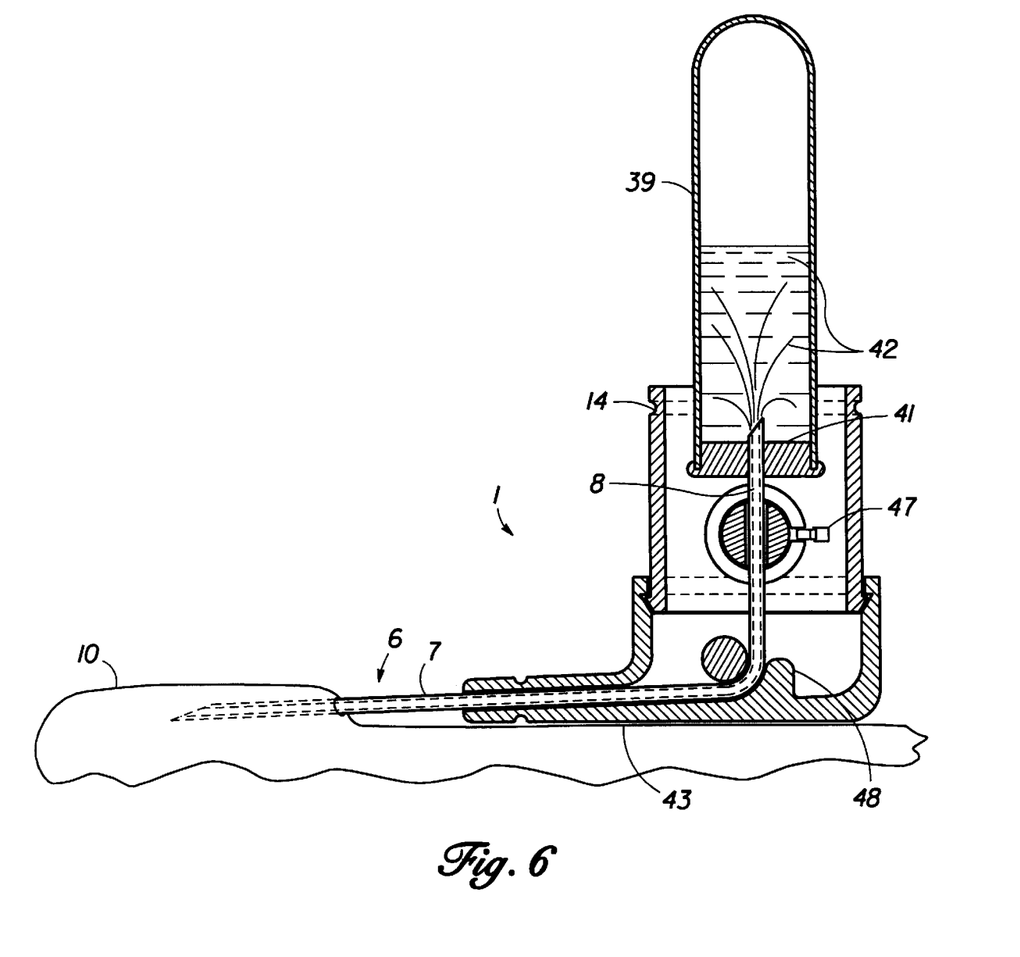
FIG. 6 is a sectional elevational view showing the device drawing blood.

Referring to FIG. 6 there is shown a sectional elevational view of the device 1 with the needle cannula 7 inserted into a body 10 and the vial insertion cannula 8 inserted into a vial 39.

The first point 37 is inserted into the body 10 which could be an arm or another part of a body wherein the first point 37 penetrates the skin and the needle cannula 7 is injected further into the body 10. The second point 40 is further inserted through the plug 41 of the vial 39 wherein blood 42 or other fluid flows from the body 10 into the cannula 6 and into the vial 39. The third end 43 of the needle cannula guide 12 is shown resting on part of the body 10 to enable the vial 39 to be placed on the vial insertion cannula 8 so the plug 41 may be pressed onto the second point 40 of the cannula 8 without moving the needle cannula 7 that is inserted into the body 10.

The cannula thrust stop 48 is shown formed on the inside of the receptor 15. The reel stop slot 47 is shown extending from the inside of the vial guide tube 14 to the outside of the vial guide tube.

Figure 7:
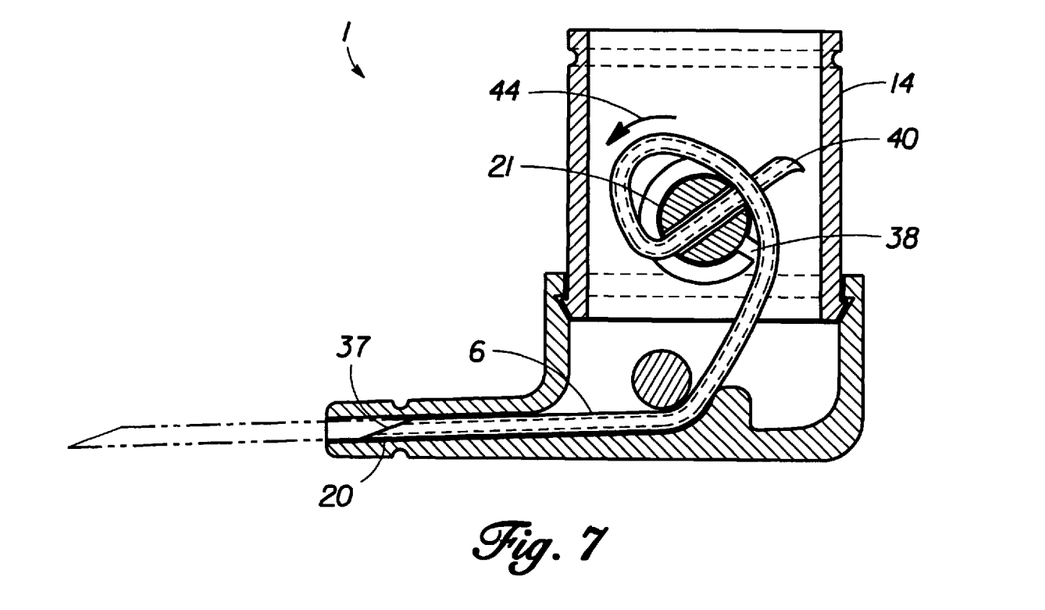
FIG. 7 is a sectional elevational view of the needle cannula destroyed.

Referring to FIG. 7 there is shown a sectional elevational view of the device 1 as the cannula 6 has been wound around the cannula reel 21.

The reel stop has been removed from the slot 38 and the biased spring 24 suitably fixed to the cannula reel 21 has caused the cannula reel 21 to rotate 44 thereby causing the cannula 6 to coil around the cannula reel 21 further pulling the first point 37 at the first end of the needle cannula 7 into the guide tunnel 20 wherein the first point cannot prick or otherwise injure a person. As the cannula 6 is coiled around the cannula reel 21, the second point 40 at the second end of the cannula 6 is further pulled into the vial guide tube 14 wherein the second point 40 may even be bent thereby preventing the second point from accidentally pricking a person or otherwise injuring someone and further causing the spread of a disease.

Figure 8:
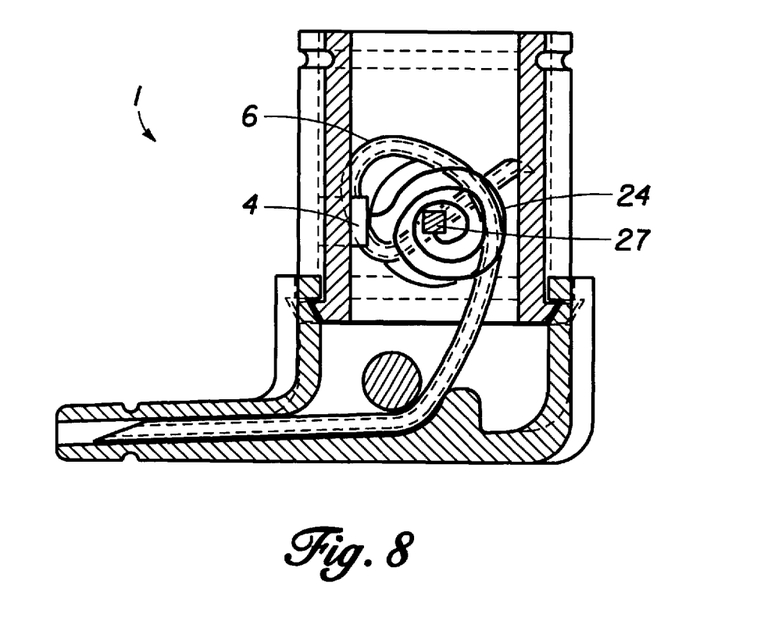
FIG. 8 is another sectional elevational view of the needle cannula destroyed.

Referring to FIG. 8 there is shown a section elevation view of the biased spring 24 as it releases its energy while coiling the cannula 6. As the biased spring 24 releases its energy, the biased spring 24 uncoils. The first end of the biased spring 24 is shown suitably fixed to the spring stop 4 and the second end of the biased spring 24 is shown suitably fixed to the axle 27.

Figure 9:
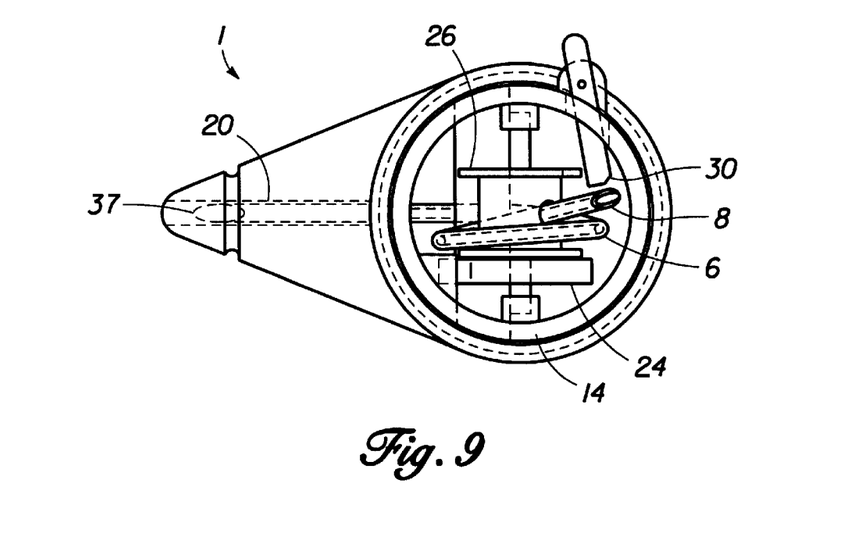
FIG. 9 is a plan view of the needle cannula destroyed.

Referring to FIG. 9 there is shown a plan view of the device 1 after the needle cannula has been drawn into the cannula guide.

The cannula 6 is shown coiled about the cannula reel 21. The biased spring 24 is shown coiled in a greater diameter than FIG. 2. The first point 37 at the first end of the needle cannula 7 is contained in the guide tunnel 20. The reel stop 30 is shown withdrawn from the slot in the second rim 26 and the second point of the vial insertion cannula 8 is bent a deeper in the vial guide tube 14 where it cannot damage, prick, or otherwise injure someone.

Figure 10:
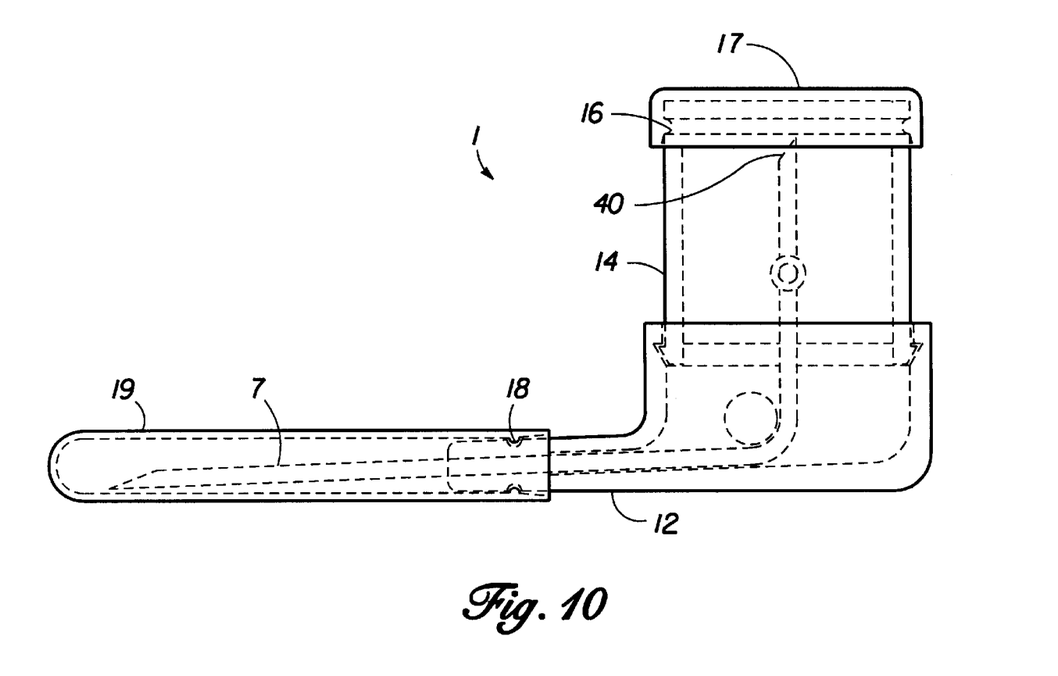
FIG. 10 is an elevational view of the device with caps on both ends.

Referring to FIG. 10 there is shown an elevational view of the device 1 with caps over the needle cannula 7 and the vial guide tube 14.

The needle cannula cap 19 is shown snapped onto the needle cannula guide tube indention 18 of the needle cannula guide 12 thereby preventing the cannula 7 from being touched or otherwise contaminated in any way. Prior to use, the needle cannula cap 19 will be pulled off the needle cannula guide 12. The guide tube cap 17 is shown suitably fixed to the outside of the vial guide tube 14 by the guide tube indentation 16. The guide tube cap 17 prevents contamination of the second point 40 of the vial insertion cannula and also prevents accidental pricking of a person from the second point during handling prior to use.

Although the system described in detail supra has been found to be most satisfactory, many variations are possible. For example two biased strings may be raised rather than one biased spring, or a rubber tube may be placed over the vial insertion cannula.

Although the invention has been described with reference to the preferred embodiment, it will be understood by those skilled in the art that additions, modifications, substitutions, deletions, and other changes not specifically described may be handled in the embodiments, and it should be understood that the details hereinabove are to be interpreted as illustrative and not in a limiting sense.

What is claimed as invention is:

1. A blood collection device adapted to be held by fingers and a thumb and supported on part of a body for inserting a needle cannula into said body and further for safely removing said needle cannula from said body and further for safely destroying a contaminated needle cannula that was in said body, said blood collection device comprising:

a hollow stem having a first end and a second end and a guide tunnel formed in said hollow stem that extends from said first end of said hollow stem that extends from said first end of said hollow stem toward said second end of said hollow stem and wherein a receptor is formed at a second end of said hollow stem, said receptor having a first end and a second end;

a vial guide tube having a first end and a second end and an inside and an outside wherein said first end of said vial guide tube is fixed to said second end of said receptor and a slot is formed in said vial guide tube between said first end and said second end;

a first socket including a hollow tube formed on said inside of said vial guide tube between said first end and said second end of said vial guide tube;

a second socket including a hollow tube formed on said inside of said vial guide tube between said first end and said second end of said vial guide tube;

an axle having a first end and a second end wherein said first end of said axle is disposed in said first socket and said second end of said axle is disposed in said second socket;

a first rim having a first side and a second side wherein the first rim is cylindrical in configuration and wherein said first rim is disposed about said first end of said axle;

a second rim having a first side and a second side wherein said second rim is cylindrical in configuration and wherein said second rim is disposed about said second end of said axle and wherein said second rim has a slot formed in said second rim wherein said slot extends from said first side of said second rim to said second side of said second rim;

a cannula reel having a first end and a second end wherein said cannula reel is cylindrical in configuration and has a third side and a fourth side wherein a hole is formed in said cannula reel that extends from said third side to said fourth side of said cannula reel and wherein said first end of said cannula reel is fixed to said second side of said first rim and said second end of said cannula reel is fixed to said first side of said second rim;

a biased spring having a first end and a second end wherein said first end of said biased spring is fixed to said inside of said vial guide tube and said second end of said biased spring is fixed to said axle;

a reel stop having a first end and a second end wherein said first end is inserted into said slot formed in said second rim and wherein said reel stop is disposed in said slot formed in said vial guide tube;

a reel stop support having a first end and a second end wherein said first end of said reel stop support is fixed to said vial guide tube and wherein a pivot pin is fixed to said reel stop support near said second end of said reel stop support;

a pivot pin wherein said pivot pin rotatably fixes said reel stop to said reel stop support;

a cannula having a first end and a second end and a bend between said first end and said second end and wherein said first end of said cannula has a first point for inserting said cannula into a body and wherein said first end of said cannula extends into said guide tunnel wherein said cannula bends and said cannula is disposed in said hole formed in said cannula reel and wherein said cannula extends from said cannula reel into said vial guide tube wherein said cannula has a second point disposed within said second end of said vial guide tube and wherein said first point on said first end of said cannula is inserted into a body wherein blood or other fluid flows from said body into said cannula and wherein said second point at said second end of said cannula is inserted through a plug at one end of a vial and said blood or other fluid flows from said body into said cannula and into said vial until said vial is sufficiently filled with said blood or said other fluid, and other vials may also be filled with blood or said other fluid wherein said second end of said reel stop is pressed with a finger or thumb causing said first end of said reel stop to be withdrawn from said slot formed in said second rim thereby allowing said biased spring to rotate said cannula reel turning said cannula around said cannula reel and further pulling said first end of said cannula and said first point of said cannula into said guide tunnel wherein said first point cannot prick or injure another person and wherein said second end of said cannula is further turned around said cannula reel thereby pulling said second point on said second end of said cannula further into said vial guide tube and damaging said second point and further preventing said second point from pricking or injuring a person or body thereby preventing the spread of HIV, hepatitis, or other diseases.

2. The blood collection device of claim 1, wherein said guide tunnel has declivity thereby facilitating the insertion and of said needle cannula into said vein or artery and further causing less damage to said vein or artery.

3. The blood collection device of claim 1 wherein a needle cannula guide tube indention is formed on said first end of said hollow stem to allow a needle cannula cap to be placed on said hollow stem to be easily removed from said needle cannula guide to keep the unused cannula sterile prior to use.

4. The blood collection device of claim 1 wherein a guide tube indention is formed on said second end of said vial guide tube thereby allowing a vial guide tube cap to be placed on said vial guide tube to be easily removed from said vial guide tube and to keep the unused second end of said cannula sterile prior to use.

5. The blood collection device of claims 1 wherein the reel stop may be released from said second rim with the use of one finger or thumb of the same hand that is holding said device.

6. The blood collection device of claim 1 wherein said device will rest on part of said body while said vial is being pressed on said second point on said second end of said cannula or thereby preventing said first end of said cannula from further injuring said body or pulling out of said vein or artery.

7. The blood collection device of claim 1 wherein said bend in said cannula is formed around a bend bar.

8. The blood collection device of claim 1 wherein said cannula is held and is supported by a cannula thrust stop to further prevent deflection of said cannula as said needle cannula is injected into a body.

* * * * *